(12) United States Patent
Berkelman

(10) Patent No.: US 7,863,048 B2
(45) Date of Patent: Jan. 4, 2011

(54) COUMARIN-BASED CYANINE DYES FOR NON-SPECIFIC PROTEIN BINDING

(75) Inventor: Thomas R. Berkelman, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 12/581,632

(22) Filed: Oct. 19, 2009

(65) Prior Publication Data

US 2010/0041163 A1 Feb. 18, 2010

Related U.S. Application Data

(63) Continuation of application No. 11/044,798, filed on Jan. 26, 2005, now Pat. No. 7,625,758.

(51) Int. Cl.
G01N 33/00 (2006.01)
C07D 405/02 (2006.01)

(52) U.S. Cl. .............................. 436/86; 546/66; 546/89; 546/99

(58) Field of Classification Search ................... 436/86; 546/66, 89, 99
See application file for complete search history.

(56) References Cited

U.S. PATENT DOCUMENTS

| | | | |
|---|---|---|---|
| 5,223,382 A | 6/1993 | Ohno | |
| 5,616,502 A | 4/1997 | Haugland et al. | |
| 5,900,376 A | 5/1999 | Das et al. | |
| 6,750,346 B2 | 6/2004 | Czerney et al. | |
| 6,972,339 B2 | 12/2005 | Lukhtanov et al. | |
| 2002/0177122 A1 | 11/2002 | Minden et al. | |
| 2003/0165942 A1 | 9/2003 | Czerney et al. | |
| 2004/0260093 A1* | 12/2004 | Czerney et al. | 546/148 |

FOREIGN PATENT DOCUMENTS

EP 1318177 B1 9/2004

OTHER PUBLICATIONS

Abd El-All, R. M. et al.; "Synthesis, Absorption Spectra Studies and Biological Activity of Some Novel Conjugated Dyes"; 2000, *Journal of the Chinese Chemical Society*, vol. 47, pp. 389-395.
Ashwell, G.J. et al.; "Improved Second-Harmonic Generation from Langmuir-Blodgett Films"; 1998, *Landmuir*, vol. 14, pp. 1525-1527.

(Continued)

*Primary Examiner*—Robert J Hill, Jr.
*Assistant Examiner*—Dwan A Gerido
(74) *Attorney, Agent, or Firm*—Townsend and Townsend and Crew LLP

(57) ABSTRACT

Protein dyes whose molecular structure is that of a coumarin moiety coupled to a quaternary ammonium heterocycle through a vinyl or polyvinyl linkage demonstrate the ability to associate with proteins in a non-covalent, non-specific manner at low pH, where the associated form displays a significantly higher fluorescence emission than the unassociated form. This makes the dyes useful as selective labels for proteins at the low pH and eliminates the need for the removal of extraneous components from the medium in which the proteins reside prior to detection.

6 Claims, 1 Drawing Sheet

OTHER PUBLICATIONS

Lehmann, Frank et al.; "Synthesis of Amphiphilic Styrylpyridinium and Styrylquinolinium Hemicyanines and Merocyanines"; 1995, *Dyes and Pigments*, vol. 29, No. 1, pp. 85-94.

Wetzl, Bianca et al.; "Set of fluorochromophores in the wavelength range from 450 to 700 nm and suitable for labeling proteins and amino-modified DNA"; 2003, *Journal of Chromatography*, vol. 793, pp. 83-92.

International Search Report and Written Opinion from PCT/US05/44378, dated Oct. 3, 2006 (8 pages).

* cited by examiner

COUMARIN-BASED CYANINE DYES FOR NON-SPECIFIC PROTEIN BINDING

CROSS-REFERENCE TO RELATED APPLICATIONS

This application is a continuation of U.S. patent application Ser. No. 11/044,798, filed Jan. 26, 2005, now allowed, the disclosure of which is herein incorporated by reference in its entirety for all purposes.

BACKGROUND OF THE INVENTION

The need to visualize proteins that are suspended in a suspending medium or matrix or dissolved in a solution or to make proteins optically detectable in general is critical to a wide range of analytical, separatory, and diagnostic procedures. Electrophoretic separations are prominent examples of procedures that rely on protein detection, and electrophoresis in its various forms finds wide use in research laboratories and clinics and in on-site monitoring of water and other environmental media and biological samples. Among the various methods of making proteins optically detectable, the attachment of fluorescent markers is particularly useful, since the signals that these markers generate are readily quantifiable and can be read, analyzed, and recorded by automated detection equipment. Fluorescent signals also allow the user or the instrument in which they are generated to control the timing and intensity of the emitted signals.

In a typical biological sample, proteins are accompanied by a range of non-protein species such as nucleic acids, polysaccharides, lipids and other small molecules. Additional non-protein components that may also be present in the suspending medium are detergents, viscosity-control agents, buffers, carrier ampholytes, reductants, and unreacted monomers. The most effective means of applying a fluorescent marking to proteins in a thorough and reliable manner that is relatively free of background signals is the attachment of a fluorescent dye to the proteins while avoiding attachment of the dye to non-protein components. To confine the dye to proteins, non-protein interfering substances can be separated out prior to application of the dye, using for example the procedure described by Das et al. in U.S. Pat. No. 5,900,376, issued May 4, 1999. Unfortunately, procedures of this kind are time-consuming, labor-intensive or incomplete. The dye can also be covalently bonded to the proteins, but the covalent bonding itself raises concerns of selectivity relative to competing reactions with other substances in the medium, in addition to concerns of reactivity and the need to assure that the reaction is complete.

In analytical procedures in which the proteins are separated from each other in a matrix such as a polyacrylamide gel for purposes of detection, the proteins once separated are typically visualized and quantified by applying a solution of a dye that will selectively bind to the proteins or that will become fluorescent or visible upon association with protein. Doing this effectively generally requires extensive washing of the matrix to remove interfering substances such as detergents, buffers, and carrier ampholytes before the dye is applied. After application of the dye, further washing is required to remove unreacted or unbound dye.

SUMMARY OF THE INVENTION

It has now been discovered that certain coumarin-based cyanine dyes associate with proteins in a manner that is both non-covalent and non-specific, and when used in media that are maintained at a low pH, display a measurable increase in fluorescence when in associated form as compared to their unassociated form. This increase in fluorescence causes the dyes to behave like selective markers, and allows them to be used effectively in protein detection and quantification with little or no need to remove other components of the medium in which the proteins are dissolved or suspended and without the need for covalent bonding between the dyes and the proteins. The dyes herein allow detection and quantification of proteins in a matrix such as a polyacrylamide gel without extensive washing prior to application of the dye, and without the need to wash away unbound dye following application.

DETAILED DESCRIPTION OF THE INVENTION AND PREFERRED EMBODIMENTS

Figure 1:
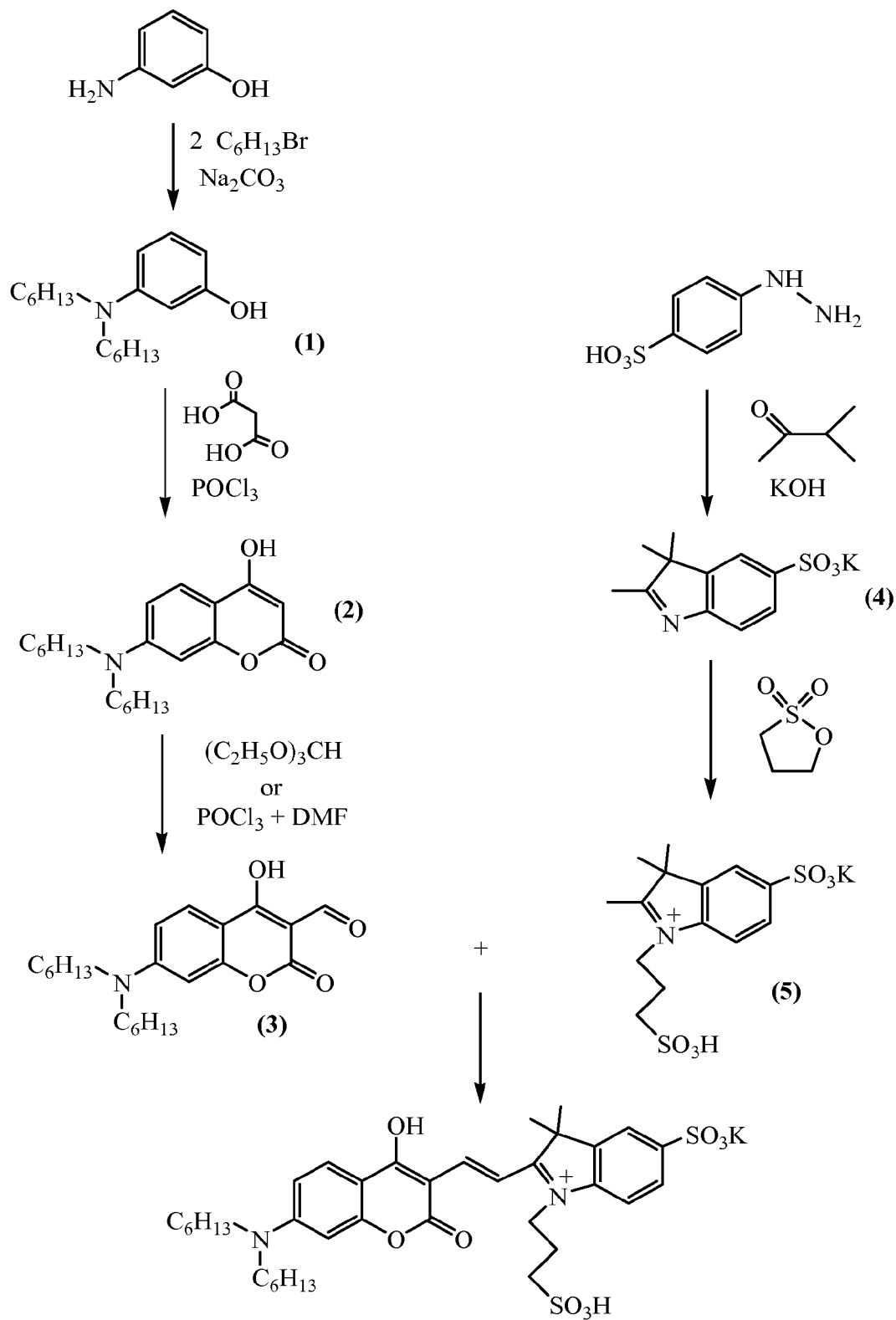
FIG. 1 is a representation of a synthetic scheme for manufacturing a compound that is representative in general of the coumarin-based cyanine dyes that are the subject of this invention.

The coumarin-based cyanine dyes that are the subject of this invention are those having the formula

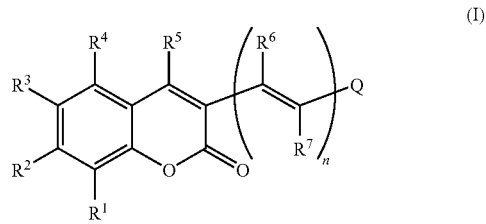

(I)

The symbols in this formula are defined as follows:

$R^1$, $R^3$, $R^4$, and $R^5$ are each either H, OH, $SO_3^-$, $C_1$-$C_{10}$ alkyl, $C_1$-$C_{10}$ alkoxy, $C_1$-$C_{10}$ alkyl substituted with halogen, or $C_1$-$C_{10}$ alkoxy substituted with halogen. These four groups are either all the same or a combination in which one or more are different from the others. The inclusion of structures in which all symbols of a particular group of symbols are the same in addition to those in which one or more are different from the others is represented in the claims hereto by the term "independently" and the phrase "independently selected from the group consisting of." This meaning applies to this term and phrase in all contexts in which they appear.

$R^2$ is either OH, $OR^{21}$, and $NR^{22}R^{23}$ wherein $R^{21}$, $R^{22}$, and $R^{23}$ are all the same, one is different from the other two, or two are different from the third, and each is either H, $C_1$-$C_{10}$ alkyl, phenyl, and substituted forms of $C_1$-$C_{10}$ alkyl and phenyl wherein the substituents are either halogen, $SO_3^-$, or combinations of halogen and $SO_3^-$. $R^{22}$ and $R^{23}$ can also be combined into a single $C_4$-$C_8$ alkyl group such that $R^2$ is a N-containing heterocycle. In the claims hereto, the phrase "a member selected from the group consisting of" when describing substituents denotes that one or more of such substituents of the group are present, and that when more than two or more are present, the substituents are either the same or a combination in which two or more of the combination differ from each other.

$R^6$ and $R^7$ are likewise either the same or different and each is either H, $C_1$-$C_{10}$ alkyl, or substituted forms of $C_1$-$C_{10}$ alkyl wherein the substituents are either halogen, $SO_3^-$, or combinations of halogen and $SO_3^-$. In further structures within the scope of this invention, $R^6$ and $R^7$ are combined as a single alkylene group, saturated or unsaturated, bridging the carbon atoms to which they are bonded to form a cyclic structure of 4, 5, 6, 7, or 8 carbon atoms.

The index n is either 0, 1, 2, 3, or 4.

The symbol Q represents a quaternary amine heterocycle of any one of the following formulas:

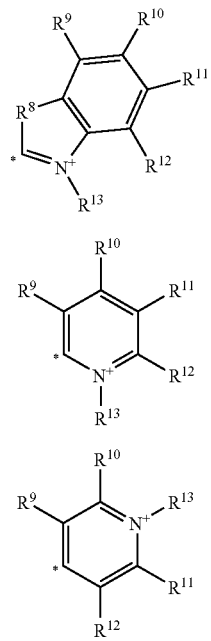

In Formulas II, III and IV, the asterisk (*) denotes the site of attachment of these groups to the location where the symbol Q is attached to the remainder of the structure in Formula I. In Formula II, furthermore, the symbol $R^8$ represents a divalent radical that is either O, S, Se, $NR^{11}$, or $CR^{82}R^{83}$, wherein any one of $R^{81}$, $R^{82}$, and $R^{83}$ are either the same as or different than the others, and each is either H, $C_1$-$C_{12}$ alkyl, $C_1$-$C_{12}$ alkyl interrupted by carbonyl (—C(=O)—), imino (—NH—), or both, $C_1$-$C_{12}$ alkyl substituted with $SO_3^-$, or $C_1$-$C_{12}$ alkyl that is both substituted with $SO_3^-$ and interrupted by carbonyl, imino, or both.

In Formulas II, III, and IV, the groups represented by the symbols $R^9$, $R^{10}$, $R^{11}$, and $R^{12}$, which as in the grouped definitions above, can be either the same or different, are each either H, OH, $SO_3^-$, methyl, or methyl substituted with halogen. In further structures within the scope of this invention, any two of $R^9$, $R^{10}$, $R^{11}$, and $R^{12}$ are combined as a single alkylene group, saturated or unsaturated, bridging the carbon atoms to which they are bonded to form a cyclic structure of 4, 5, 6, 7, or 8 carbon atoms.

Still further in Formulas II, III, and IV, $R^{13}$ is either $C_1$-$C_{20}$ alkyl or $C_1$-$C_{20}$ alkyl substituted with $CO_2^-$, $SO_3^-$, or both.

For each of the symbols in Formulas I, II, III, and IV, certain portions of the full scope set forth above are preferred. The symbol $R^5$ is preferably either H, OH, $C_1$-$C_4$ alkyl, or $C_1$-$C_4$ alkoxy. Among these, OH and $C_1$-$C_4$ alkoxy are more preferred, and OH is the most preferred. Furthermore, $R^1$, $R^3$, $R^4$, and $R^5$ are preferably not all the same, and in many embodiments of the invention, $R^5$ differs from $R^1$, $R^3$, and $R^4$. Among these embodiments, a preferred group is that in which $R^1$, $R^3$, and $R^4$ are each H. The symbol $R^2$ is preferably OH, $C_1$-$C_{10}$ alkoxy, or $NR^{22}R^{23}$ wherein $R^{22}$ and $R^{23}$ are independently $C_1$-$C_{10}$ alkyl, and among these, $C_1$-$C_{10}$ alkoxy and $NR^{22}R^{23}$ are more preferred, with $NR^{22}R^{23}$ the most preferred. The scope of $R^{13}$ has certain preferences as well. Preferred groups for $R^{13}$ are $C_5$-$C_{20}$ alkyl and $C_2$-$C_{10}$ alkyl substituted with $CO_2^-$, $SO_3^-$, or both. Preferred values for n are 1 and 2, with 2 the most preferred.

Within the formulas for the quaternary amine heterocycle represented by the symbol Q, preferences exist as well. The divalent radical $R^8$, which appears only in Formula II, is preferably either O, $NR^{81}$, or $CR^{82}R^{83}$, more preferably either $NR^{81}$ or $CR^{82}R^{83}$, and most preferably $CR^{82}R^{83}$. One preferred structure for $CR^{82}R^{83}$ is $C(CH_3)_2$. In certain structures within the scope of this invention, the groups represented by symbols $R^{82}$ and $R^{83}$ are different, and among these, $R^{82}$ is preferably the methyl group and $R^{83}$ is preferably $C_1$-$C_{12}$ alkyl interrupted by carbonyl, imino, or both, $C_1$-$C_{12}$ alkyl substituted with $SO_3^-$, and $C_1$-$C_{12}$ alkyl that is both substituted with $SO_3^-$ and interrupted by carbonyl, imino, or both. One preferred structure for $R^{33}$ is $(CH_2)_3$—C(=O)—NH—$(CH_2)_3$—$SO_3^-$. Of the groups represented by the symbols $R^9$, $R^{10}$, $R^{11}$, and $R^{12}$, it is preferred that at least one such group is $SO_3^-$, and it is particularly preferred that one is $SO_3^-$ and the remainder are all H. For the symbol Q in general, preferred formulas are Formulas II and IV, and the most preferred is Formula II.

In the practice of the present invention, the dyes can be used for detecting proteins in a medium having a pH of 5 or below, by contacting the medium with the dyes while maintaining the pH of the medium at 5 or below. A preferred pH range is 1 to 5, and a particularly preferred range is 2 to 5. The medium is preferably an aqueous medium, and can be a gel or a liquid solution. The dyes are useful in detecting both precipitated proteins suspended in the medium and proteins dissolved in the medium. The medium can be a stationary medium such as a motionless gel in a slab-shaped electrophoresis cell or a stationary tube or capillary, or a mobile medium such as solutes dissolved in a carrier liquid passing through a tube or capillary.

The dye is preferably applied as a liquid solution, and most preferably an aqueous liquid solution. Optional components in the solution other than the dye are: (1) a water-miscible organic component (such as for example methanol, ethanol, 1- or 2-propanol, ethylene glycol, propylene glycol, glycerol, acetonitrile, dimethyl sulfoxide, formamide, dimethylformamide, diglyme, triglyme, or tetraglyme) at a concentration of up to 50% (on a volume basis), (2) an acid component (such as for example acetic acid, formic acid, lactic acid, propionic acid, phosphoric acid, trichloroacetic acid, trifluoroacetic acid, citric acid, oxalic acid, or hydrochloric acid) at a concentration of up to 20% (on a volume basis), (3) a buffer (such as for example sodium phosphate, sodium acetate, sodium formate, or sodium citrate) at a pH of from 1 to 6 and a concentration of from 5 to 200 mM, and (4) a detergent (examples of which are sodium dodecyl sulfate, TRITON® X-100, SB3-10, and TWEEN® 20) at a concentration of from 0.005% to 1% (on a weight/volume basis). The concentration of the dye in the solution can vary and is not critical to the invention, although most efficient and economical results will generally be achieved with concentrations within the range of from about 50 nM to about 10 μM. Application of the dye to the medium is readily achieved by conventional means for staining media, such as immersion of the medium in a solution of the dye or purging of a container or flow-through receptacle in which the medium is retained with the dye solution.

Detection of the presence of the proteins and the relative amounts of each is then achieved by conventional means of excitation and of the collection and processing of fluorescent emission. Excitation can be achieved for example by irradiating the medium with light from a light source capable of producing light at or near the wavelength of the maximum absorption of the dye. Examples of suitable light sources are ultraviolet or visible wavelength lamps, mercury arc lamps, xenon arc lamps, argon lasers, and YAG (yttrium-aluminum-garnet) lasers. Excitation can be performed by trans-illumination or epi-illumination. Preferred light sources are those that produce light at a wavelength between 300 and 650 nm. Laser scanners, fluorescence microtiter plate readers, fluorometers, gel readers, and chromatographic detectors are examples of suitable light sources. Once the dye has been excited, the emitted fluorescence can be detected by conventional means as well, examples of which are CCD cameras, photographic film, photodiodes, quantum counters, scanning microscopes, and the various types of equipment listed above as light sources with incorporated detection components.

Reaction schemes for synthesis for the dyes of the present invention are illustrated by the representative example shown in FIG. 1. In the dye of this example, $R^1$, $R^3$, $R^4$, $R^6$, and $R^7$ are H, $R^2$ is $(C_6H_{13})_2N$, $R^5$ is OH, n is 1, and Q is Formula II in which $R^8$ is $(CH_3)_2C$, $R^9$, $R^{11}$, and $R^{12}$ are H, $R^{10}$ is $SO_3$, and $R^{13}$ is sulfonatopropyl ($^-O_3S$—$(CH_2)_3$). Each of the reactions shown in the FIGURE is known in the art and published in the literature. The reaction to produce intermediate (1) is disclosed for example by Crossley, M. L., et al., *Journal of the American Chemical Society* 74: 573-578 (1952); the reaction to produce intermediate (2) is disclosed by Knierzinger, A., et al., *Journal of Heterocyclic Chemistry* 17: 225-229 (1980); the reactions to produce intermediate (3) are disclosed by Rahman, M.-U., et al., *Indian Journal of Chemistry* 29B: 941-943 (1990) and El-Aal, R. M. A., et al., *Journal of the Chinese Chemical Society* 47: 389-395 (2000); the reactions to produce intermediates (4) and (5) are disclosed by Mujumdar, R. B., et al., *Bioconjugate Chemistry* 4: 105-111 (1993); and the final reaction to produce the dye is disclosed by Czerney et al., United States Published Patent Application No. US 2003/0165942 A1, published Sep. 4, 2003. Other dyes within the scope of the present invention can be synthesized by analogous reaction schemes that will be readily apparent to the skilled synthesis chemist.

The invention is illustrated by the following examples.

EXAMPLES

Example 1

Effect of Protein on Fluorescence of Coumarin-Based Cyanine Dyes

A series of coumarin-based cyanine dyes within the scope of Formula I above were tested by the following procedure. A 20 mg/mL solution of denatured protein (yeast alcohol dehydrogenase or bovine carbonic anhydrase in 8 M urea) was diluted 100-fold into 50 mM sodium formate pH 4.0 to a final concentration of 0.2 mg/mL. Dye was added from a DMSO stock solution (0.4-1 mM) to a final concentration of 200 nM. The resulting mixture was incubated at room temperature for at least 15 minutes and fluorescence readings were taken on an Aminco Bowman Series 2 Luminescence spectrometer with the excitation and emission monochrometers set at the absorbance and emission maxima, respectively, for each dye. The spectrometer slit width was set at 4 nm. Fluorescence readings at the same wavelengths were also taken of each dye diluted identically into buffer without added protein.

The peak fluorescence intensities measured in the presence of 0.2 mg/mL protein at pH 4 are shown in the table below, which lists both the peak intensity when associated with protein and the ratio of the intensity of the dye-protein complex and the intensity of the protein-free dye. The peak intensities are expressed in arbitrary units, and the values shown have significance relative to each other only.

| No. | Structure | Peak | Ratio |
|---|---|---|---|
| 1 | 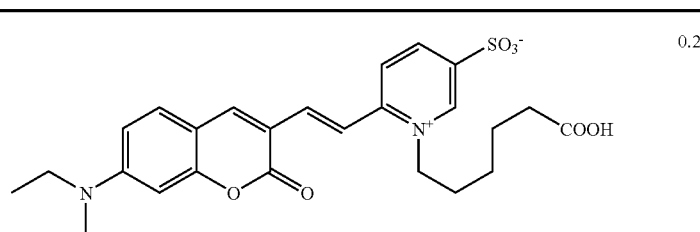 | 0.2 | 5.88 |
| 2 | 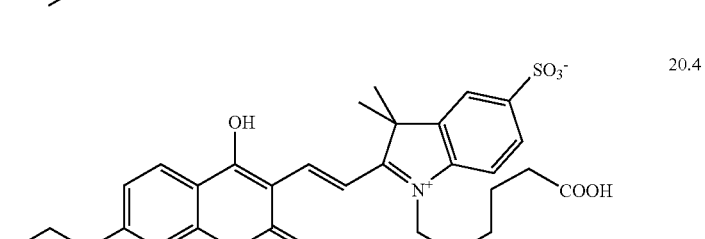 | 20.4 | ~1500 |

-continued
| No. | Structure | Peak | Ratio |
|---|---|---|---|
| 3 | 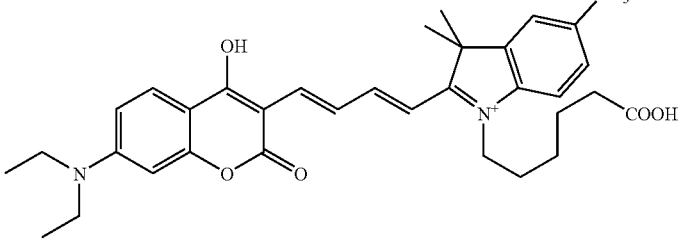 | 23.7 | ~800 |
| 4 | 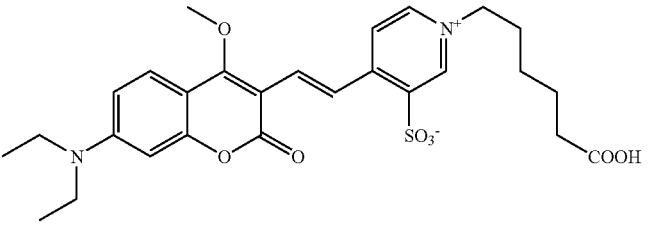 | 0.7 | 233 |
| 5 | 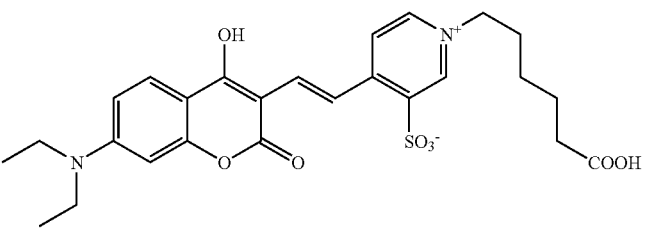 | 5.2 | 740 |
| 6 | 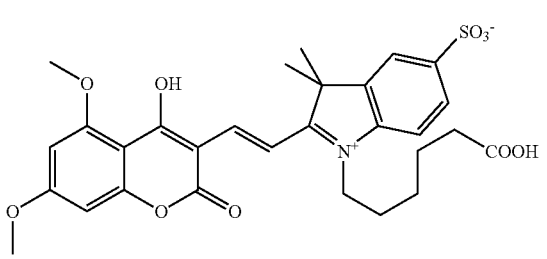 | 15.0 | 16.5 |
| 7 | 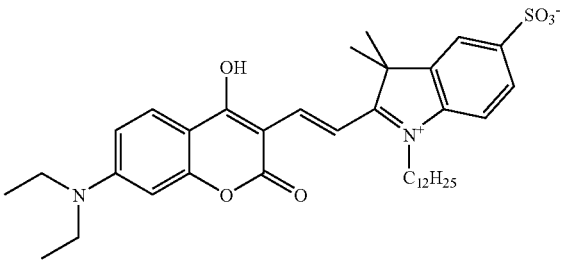 | 15.6 | 124 |
| 8 | 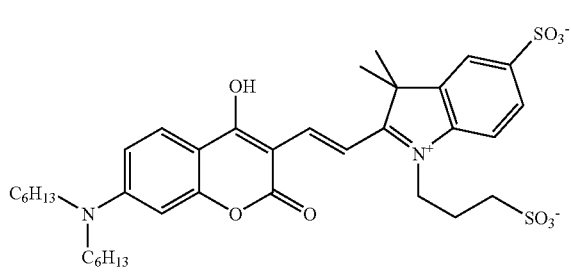 | 12.6 | 140 |

-continued

| No. | Structure | Peak | Ratio |
|---|---|---|---|
| 10 | 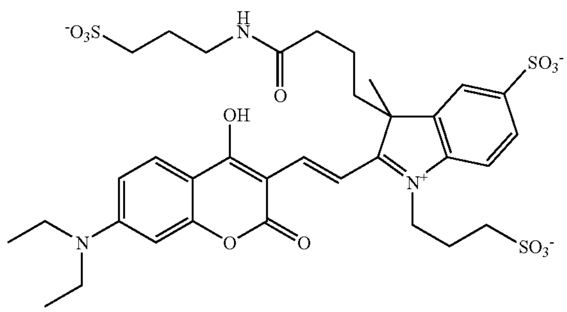 | 16.2 | 54 |
| 11 | 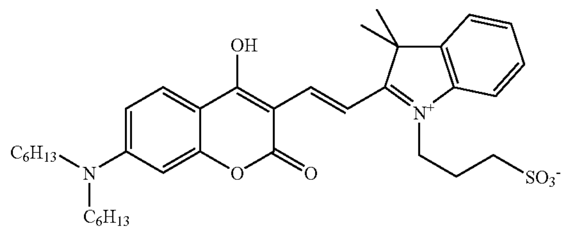 | 19.5 | 250 |

Example 2

Use of Coumarin-Based Cyanine Dye for Staining 1-D SDS-PAGE Gel

An 18-well 4-20% Tris-Cl gel (Criterion® System of Bio-Rad Laboratories, Inc., Hercules, Calif., USA) was loaded with serial dilutions of broad range SDS-PAGE standards (Bio-Rad Laboratories, Inc.) and subjected to electrophoresis according to the manufacturer's instructions. The dilutions and the lanes in the gel in which each dilution was placed were as listed below:

| Lane No. | Load (ng of each protein) |
|---|---|
| 1 | (blank) |
| 2 | 960 |
| 3 | 480 |
| 4 | 240 |
| 5 | 120 |
| 6 | 60 |
| 7 | 30 |
| 8 | 15 |
| 9 | 8 |
| 10 | 4 |
| 11 | 2 |
| 12 | 1 |
| 13 | 0.5 |
| 14 | 0.25 |
| 15 | 0.125 |

The gel was fixed for 16.5 hours in 300 mL of 40% (volume/volume) ethanol and 10% (volume/volume) acetic acid. Following the fixing step, the gel was strained in 125 mL of a solution consisting of 0.2 µM of Compound 8 of Example 1 in 30% (volume/volume) methanol and 1% (volume/volume) oxalic acid. After 2 hours and without washing of the gel after the application of Compound No. 8, the gel was scanned on an FX fluorescence scanner (Bio-Rad Laboratories, Inc.) using a 532 nm laser and a 605 nm bp 50 nm emission filter. The scan showed distinct, clearly delineated bands for the various proteins through lane no. 11, with some of the bands still visible in lanes 12 through 14.

Example 3

Use of Coumarin-Based Cyanine Dye for Staining 2-D Gel

Immobilized pH gradient strips (ReadyStrip® IPG strips, 11 cm pH 3-10 NL, Bio-Rad Laboratories, Inc.) were loaded with 40 µg of *E. coli* protein in 8 M urea, 2% CHAPS, 40 mM dithiothreitol, 0.2% (weight/volume) Bio-Lyte ampholyte pH 3-10 (Bio-Rad Laboratories, Inc.). First-dimension isoelectric focusing followed by equilibration and second-dimension of SDS-PAGE were performed as described in the ReadyStrip® instruction manual. Criterion® 8-16% Tris-Cl gels (Bio-Rad Laboratories, INc.) were used for the second dimension. The resulting 2-dimensional gels were fixed for 1 hour in 170 mL per gel of 40% (volume/volume) ethanol and 10% (volume/volume) acetic acid, and stained with 200 mL of a solution consisting of 0.2 µM of Compound 8 of Example 1 in 30% (volume/volume) methanol and 7% (volume/volume) acetic acid. After 2 hours and without washing of the gel after the application of Compound No. 8, the gel was scanned on an FX fluorescence scanner (Bio-Rad Laboratories, Inc.), using a 532 nm laser and a 605 nm bp 50 nm emission filter. The scan showed distinct, clearly delineated spots in a two-dimensional array.

Example 4

Use of Coumarin-Based Cyanine Dye for Quantification of Protein in the Presence of Detergent, Carrier Ampholyte and Reductant Frozen rat liver was ground and extracted with a solution consisting of 9 M urea, 4% CHAPS, 40 mM dithiothreitol, and 0.2% (weight/volume) Bio-Lyte. Dilutions of the extract were made in the same solution to relative concentrations of 0.5×, 0.25×, 0.125×, and 0.05×. Standard proteins (lactoglobulin and myoglobin) were dissolved in the same solution to concentrations of 2 mg/mL, 1 mg/mL, 0.5 mg/mL, 0.25 mg/mL, 0.125 mg/mL, and 0.1 mg/mL. Each protein sample (rat liver extract as well as standard proteins) was diluted 50-fold with an assay solution consisting of 2 µM of Compound 2 of Example 1, in 50 mM sodium formate buffer at pH 4. A 50-fold dilution of the extraction solution was also made to serve as the assay zero point. Following incubation at room temperature for 15 minutes and without washing of the gel after the application of Compound No. 2, each sample was read in a fluorescence microplate reader with the excitation set at 495 nm and the emission set at 535 nm. The data for relative fluorescence intensity vs. dilution factor (prior to dilution with the assay buffer) for the rat liver extract showed a linear relation ranging from approximately 1,000 arbitrary fluorescence units at zero dilution factor to approximately 17,000 units at 0.5×. The data for relative fluorescence intensity vs. the protein concentration (prior to dilution into the assay buffer) for the standard proteins, using a linear regression analysis likewise showed a linear relation ranging from zero mg/mL of protein to 2 mg/mL of protein for both proteins.

The foregoing is offered for purposes of illustration. Further variations, modifications, and substitutions that fall within the scope of the invention will be readily apparent to those skilled in the art.

What is claimed is:

1. A compound of the formula:

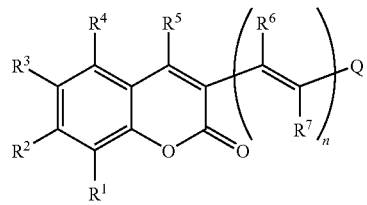

wherein:

$R^1$, $R^3$, and $R^4$ are all H;

$R^5$ is OH;

$R^2$ is $NR^{22}R^{23}$ wherein $R^{22}$ and $R^{23}$ are $C_1$-$C_{10}$ alkyl, or $R^{22}$ and $R^{23}$ are combined to form a single $C_4$-$C_8$ alkyl group such that $R^2$ is a N-containing heterocycle;

$R^6$ and $R^7$ are H;

n is 1; and

Q is

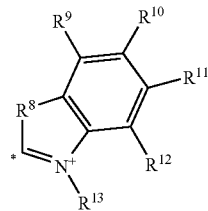

where * denotes the site of attachment, $R^8$ is $CR^{82}R^{83}$ wherein $R^{82}$ is $CH_3$ and $R^{83}$ is a member selected from the group consisting of $CH_3$ and $(CH_2)_3$—C(~O)—NH—$(CH_2)_3$—$SO_3^-$, $R^9$, $R^{11}$, and $R^{12}$ are H, $R^{10}$ is $SO_3^-$, and $R^{13}$ is $C_1$-$C_{20}$ alkyl substituted with $SO_3^-$.

2. The compound of claim 1, wherein
$R^2$ is $NR^{22}R^{23}$ wherein $R^{22}$ and $R^{23}$ are $C_1$-$C_{10}$ alkyl; and
$R^8$ is $CR^{82}R^{83}$ wherein $R^{82}$ is $CH_3$ and $R^{83}$ is $CH_3$.

3. The compound of claim 1, having the formula:

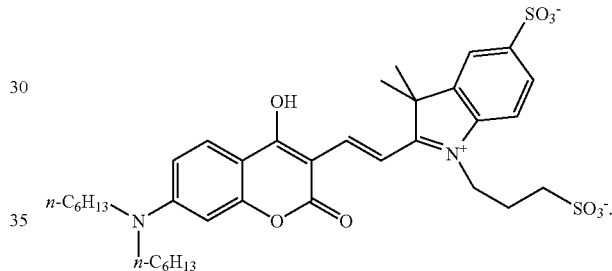

4. The compound of claim 1, having the formula:

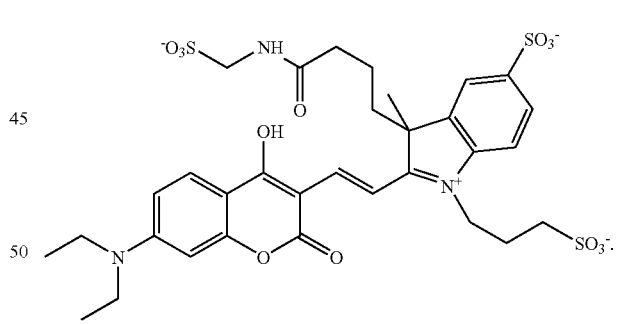

5. A composition comprising a compound of claim 1 and an acid.

6. The composition of claim 5, wherein the acid is selected from the group consisting of oxalic acid and acetic acid.

* * * * *